United States Patent
Fuglsang et al.

(12)

(10) Patent No.: US 6,207,149 B1
(45) Date of Patent: Mar. 27, 2001

(54) STARCH BINDING DOMAINS (SBDS) FOR ORAL CARE PRODUCTS

(75) Inventors: Claus Crone Fuglsang, Niva; Rie Tsuchiya, Birkerod, both of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/276,071

(22) Filed: Mar. 25, 1999

Related U.S. Application Data

(63) Continuation of application No. PCT/DK97/00446, filed on Oct. 13, 1997.

(30) Foreign Application Priority Data

Oct. 11, 1996 (DK) .................................................. 1128/96

(51) Int. Cl.[7] .......................... A61K 38/43; A61K 38/54; C12N 9/00; C12N 9/24; C12N 9/46
(52) U.S. Cl. ........................ 424/94.1; 424/94.2; 435/183; 435/200; 435/202; 435/211; 435/219
(58) Field of Search ............................... 435/202; 424/49, 424/50, 94.1, 94.3, 94.61

(56) References Cited

PUBLICATIONS

Diderichsen et al. cloning of a maltogenic alpha–amylase from *B. stearothermophilus*. FEMS Microbiiology Letters, 1988, vol. 56:53–60.*
Hayashida et al. Structure of the raw–starch–affinity site on the Aspergillus awamori var. kawachi glycoamylase I molecule. Agric. Biol. Chem.; 1989, vol. 53(1):135–141.*
Tomme et al., American Chemical Society, Chapter 10, pp. 142–161 (1995).
Ong et al., Tibtech, vol. 7, pp. 239–243 (Sep. 1989).
Svensson et al., (1989) Biochem. J. 264(15):309
Belshaw et al., (1990) Febs 269(2):350.
Le Gal–Coeffet et al., (1995) 233:561.

* cited by examiner

*Primary Examiner*—Rebecca E. Prouty
*Assistant Examiner*—Manjunath Rao
(74) *Attorney, Agent, or Firm*—Elias J. Lambiris, Esq.; Reza Green, Esq.

(57) ABSTRACT

The present invention relates to an oral care composition comprising a Starch Binding Domain and further ingredients conventionally used in oral care compositions, oral care products, and the use of SBDs for oral care purposes.

8 Claims, No Drawings

SEQUENCE LISTING

```
<160> NUMBER OF SEQ ID NOS: 7

<210> SEQ ID NO 1
<211> LENGTH: 327
<212> TYPE: DNA
<213> ORGANISM: Steatotermophilus

<400> SEQUENCE: 1
agtggaacgc agacatcggt tgtgtttact gtgaaaagtg cgcctccgac caacctgggg      60
gataagattt acctgacggg caacataccg gaattgggga attggagcac ggatacgagc     120
ggagccgtta acaatgcgca agggcccctg ctcgcgccca attatccgga ttggttttat     180
gtattcagcg ttccagcagg aaagacgatt caattcaagt tcttcatcaa gcgtgcggat     240
ggaacgattc aatgggagaa tggttcgaac cacgtggcca caactcccac gggtgcaacc     300
ggtaacatta ctgttacgtg gcaaaac                                         327

<210> SEQ ID NO 2
<211> LENGTH: 109
<212> TYPE: PRT
<213> ORGANISM: Steatotermophilus

<400> SEQUENCE: 2

Ser Gly Thr Gln Thr Ser Val Val Phe Thr Val Lys Ser Ala Pro Pro
1               5                   10                  15

Thr Asn Leu Gly Asp Lys Ile Tyr Leu Thr Gly Asn Ile Pro Glu Leu
            20                  25                  30

Gly Asn Trp Ser Thr Asp Thr Ser Gly Ala Val Asn Asn Ala Gln Gly
        35                  40                  45

Pro Leu Leu Ala Pro Asn Tyr Pro Asp Trp Phe Tyr Val Phe Ser Val
    50                  55                  60

Pro Ala Gly Lys Thr Ile Gln Phe Lys Phe Phe Ile Lys Arg Ala Asp
65                  70                  75                  80
```

Gly Thr Ile Gln Trp Glu Asn Gly Ser Asn His Val Ala Thr Thr Pro
                85                  90                  95

Thr Gly Ala Thr Gly Asn Ile Thr Val Thr Trp Gln Asn
            100                 105

<210> SEQ ID NO 3
<211> LENGTH: 576
<212> TYPE: DNA
<213> ORGANISM: Steatotermophilus

<400> SEQUENCE: 3
tccgcttcag cgccgcaaat cggatcggtt gctccaaata tggggattcc gggtaatgtg     60
gtcacgatcg acgggaaagg ttttgggacg acgcaggaa ccgtgacatt tggcggagtg    120
acagcgactg tgaaatcctg acatccaat cggattgaag tgtacgttcc caacatggcc    180
gccgggctga ccgatgtgaa agtcaccgcg ggtggagttt ccagcaatct gtattcttac    240
aatattttga gtggaacgca gacatcggtt gtgtttactg tgaaaagtgc gcctccgacc    300
aacctggggg ataagattta cctgacgggc aacataccgg aattggggaa ttggagcacg    360
gatacgagcg gagccgttaa caatgcgcaa gggcccctgc tcgcgcccaa ttatccggat    420
tggttttatg tattcagcgt tccagcagga agacgattca aattcaagtt cttcatcaag    480
cgtgcggatg gaacgattca atgggagaat ggttcgaacc acgtggccac aactcccacg    540
ggtgcaaccg gtaacattac tgttacgtgg caaaac                              576

<210> SEQ ID NO 4
<211> LENGTH: 192
<212> TYPE: PRT
<213> ORGANISM: Steatotermophilus

<400> SEQUENCE: 4

Ser Ala Ser Ala Pro Gln Ile Gly Ser Val Ala Pro Asn Met Gly Ile
1               5                   10                  15

Pro Gly Asn Val Val Thr Ile Asp Gly Lys Gly Phe Gly Thr Thr Gln
            20                  25                  30

Gly Thr Val Thr Phe Gly Gly Val Thr Ala Thr Val Lys Ser Trp Thr
        35                  40                  45

Ser Asn Arg Ile Glu Val Tyr Val Pro Asn Met Ala Ala Gly Leu Thr
    50                  55                  60

Asp Val Lys Val Thr Ala Gly Gly Val Ser Ser Asn Leu Tyr Ser Tyr
65                  70                  75                  80

Asn Ile Leu Ser Gly Thr Gln Thr Ser Val Val Phe Thr Val Lys Ser
                85                  90                  95

Ala Pro Pro Thr Asn Leu Gly Asp Lys Ile Tyr Leu Thr Gly Asn Ile
            100                 105                 110

Pro Glu Leu Gly Asn Trp Ser Thr Asp Thr Ser Gly Ala Val Asn Asn
        115                 120                 125

Ala Gln Gly Pro Leu Leu Ala Pro Asn Tyr Pro Asp Trp Phe Tyr Val
    130                 135                 140

Phe Ser Val Pro Ala Gly Lys Thr Ile Gln Phe Lys Phe Ile Lys
145                 150                 155                 160

Arg Ala Asp Gly Thr Ile Gln Trp Glu Asn Gly Ser Asn His Val Ala
                165                 170                 175

Thr Thr Pro Thr Gly Ala Thr Gly Asn Ile Thr Val Thr Trp Gln Asn
            180                 185                 190

-continued

```
<210> SEQ ID NO 5
<211> LENGTH: 34
<212> TYPE: DNA
<213> ORGANISM: Artificial Sequence
<220> FEATURE:
<223> OTHER INFORMATION: Primer #110755

<400> SEQUENCE: 5
gatgctgcag cagcggcgtc cgcttcagcg ccgc                        34

<210> SEQ ID NO 6
<211> LENGTH: 36
<212> TYPE: DNA
<213> ORGANISM: Artificial Sequence
<220> FEATURE:
<223> OTHER INFORMATION: Primer #110756

<400> SEQUENCE: 6
gatgctgcag cagcggcgag tggaacgcag acatcg                      36

<210> SEQ ID NO 7
<211> LENGTH: 33
<212> TYPE: DNA
<213> ORGANISM: Artificial Sequence
<220> FEATURE:
<223> OTHER INFORMATION: Primer #110757

<400> SEQUENCE: 7
gatggaattc ggatcctcca tatgtactac tcc                         33
```

STARCH BINDING DOMAINS (SBDS) FOR ORAL CARE PRODUCTS

CROSS-REFERENCE TO RELATED APPLICATIONS

This application is a continuation application of PCT/DK97/00446 filed Oct. 13, 1997 and claims priority under 35 U.S.C. 119 of Danish application no. 1128/96 filed Oct. 11, 1996, the contents of which are fully incorporated herein by reference.

FIELD OF THE INVENTION

The present invention relates to an oral care composition comprising a Starch Binding Domain, an oral care product comprising an oral care composition of the invention, and further to the use of a Starch Binding Domain for oral care purposes, including prevention of the formation of dental plaque and/or removal of dental plaque.

BACKGROUND OF THE INVENTION

The formation of dental plaque leads to dental caries, gingival inflammation, periodontal disease, and eventually tooth loss. Dental plaque is a mixture of bacteria, epithelial cells, leukocytes, macrophages, and other oral exudate. Said bacteria produce highly branched polysaccharides which together with microorganisms from the oral cavity form an adhesive matrix for the continued proliferation of dental plaque.

As dental plaque continues to accumulate rock hard white or yellowish deposits arise. These deposits are called calcified plaque, calculus or tartar, and are formed in the saliva from plaque and minerals, such as in particular calcium.

Oral Polysaccharides

Oral polysaccharides mainly consist of the adhesive polysaccharides termed "fructans" and "glucans".

Glucans are produced from carbohydrates, such as sucrose introduced into the mouth, e.g. as a food or beverage constituent, by the action of cariogenic microorganisms, such as *Streptococcus mutans* or *Streptococcus sanguis*, growing in the oral cavity.

The term "glucan" is a general common term covering a number of polysaccharides and includes cellulose, starch, dextran, mutan, pullulan etc.

Oral glucans comprise water-soluble dextran, having large portions of α-1,6 glucosidic linkage and as the major component a water-insoluble extra-cellular polysaccharide called "mutan" comprised of a backbone with α-1,3-glycosidic linkages and branches with α-1,6-glycosidic linkages.

Mutan binds to almost any surface such as the surface of teeth, (i.e. hydroxyapatite constituting the hard outer porous layer of the teeth), pellicle, the cell surface of oral microorganisms as well as to acceptor proteins on the cell of said cariogenic bacteria adhering to the teeth surface.

WO 95/31556 (Unilever) discloses an oral composition comprising the Glucan Binding Domain of glycosyltransferase having specific binding affinity for dextran (being a polysaccharide with mainly α-1,6-glucosidic linkages).

According to WO 95/31556 the Glucan Binding Domain is covalently chemically bound to material having an activity, such as inhibitory effect against the formation of dental plaque. The material may be an enzyme, such as galactose oxidase (see Example 6 of said WO application).

A number of Cellulose Binding Domains are known in the art. Peter Tomme et al., (1996), "Cellulose-Binding Domains: Classification and Properties" in "Enzymatic Degradation of Insoluble Carbohydrates", John N. Saddler and Michael H. Penner (Eds.), ACS Symposium Series, No. 618; Ong et al. (1989), TIBTech 7, p. 239–243; and WO 93/21331 describe a vast number of Cellulose Binding Domains.

SUMMARY OF THE INVENTION

It is the object of the present invention to provide oral care products which can be used for improving the oral hygiene of humans and animals, by effectively preventing the formation of dental plaque and/or removing already deposited dental plaque.

The present inventors have seen indications that Starch Binding Domains (SBDs) have a dispersing effect on oral polysaccharides. Consequently, Starch Binding Domains are suitable for removing and/or preventing dental plaque.

Starch Binding Domains (SBD)

In the following "Starch Binding Domain" will be abbreviated as "SBD" and is meant to define all polypeptide sequences or peptide sequences having affinity for binding to Starch.

Most known SBDs today are found in CGTases, i.e. cyclodextrin glucanotransferases (E.C. 2.4.1.19), and glucoamylases (E.C. 3.2.1.3). See also Chen et al. (1991), Gene 991, p. 121–126, describing Starch Binding Domain hybrids.

Specifically, an SBD has been found in the commercially available enzyme AMG (a glucoamylase) from *Aspergillus niger*.

SBDs may be useful as a single domain polypeptide or as a dimer, a trimer, or a polymer; or as a part of a protein hybrid.

Single Unit Starch Binding Domain (Single Unit SBD)

The term "Single Unit SBD" may also be referred to as "Isolated SBD" or "Separate SBD".

In the context of the present invention a "Single Unit SBD" includes up to the entire part of the amino acid sequence of an SBD-containing enzyme, e.g. a polysaccharide hydrolyzing enzyme, being essentially free of the catalytic domain, but retaining the SBD(s).

Thus, in the context of the invention, the entire catalytic amino acid sequence of a starch degrading enzyme (e.g. a glucoamylase) or other enzymes comprising one or more SBDs is not to be regarded as a Single Unit SBD.

Typically a Single Unit SBD constitutes one or more SBDs of a polysaccharide hydrolyzing enzyme, one or more SBDs of a starch binding protein or a protein designed and/or engineered to be capable of binding to starch.

The Single Unit SBD is at least as large as the minimum number of amino acids in the amino acid sequence required to bind to starch.

A Single Unit SBD may also be an amino acid sequence in which the binding and catalytic domain are one and the same.

Isolation of a Starch Binding Domain

In order to isolate the Starch Binding Domain of e.g. a glucoamylase, several genetic approaches may be used. One method uses restriction enzymes to remove a portion of the gene and then to fuse the remaining gene-vector fragment in frame to obtain a mutated gene that encodes a protein truncated for a particular gene fragment. Another method involves the use of exonucleases such as Ba131 to systematically delete nucleotides either externally from the 5' and the 3' ends of the DNA or internally from a restricted gap within the gene. These gene deletion methods result in a mutated gene encoding a shortened gene molecule which may then be evaluated for substrate binding ability. Appropriate substrates for evaluating the binding activity include compounds such as starch.

Once a nucleotide sequence encoding the substrate binding region has been identified, either as cDNA or chromosomal DNA, it may then be manipulated in a variety of ways to fuse it to a DNA sequence encoding the enzyme of interest. The starch binding encoding fragment and the DNA encoding the enzyme of interest are then ligated with or without a linker. The resulting ligated DNA may then be manipulated in a variety of ways to provide for expression. Microbial hosts such as Aspergillus, e.g., *A. niger* and *A. oryzae*, Bacillus, *E. coli* or *S. cerevisiae* are preferred.

In the first aspect, the invention relates to an oral care composition comprising an SBD and ingredients conventionally used in oral care compositions.

The SBD may be any SBD, such as a Single Unit SBD of any kind. SBDs specifically contemplated are SBDs isolated from microorganisms, such as bacteria, filamentous fungi or yeasts, such as SBDs derived from e.g. a strain of Aspergillus sp. especially *A. niger*.

Example 1 below describes the cloning and expression of an SBD as being a region in the maltogenic amylase enzyme product produced by *Bacillus stearothermophilus* C599 disclosed in EP patent no. 120,693 (Novo Industri A/S).

In an embodiment of the invention the oral care composition further comprises an enzyme capable of degrading polysaccharides.

In the second aspect, the invention relates to an oral care product comprising an oral care composition of the invention.

In the third aspect, the invention relates to the use of an SBD for oral care purposes, including preventing the formation of dental plaque and/or removing dental plaque.

DETAILED DESCRIPTION OF THE INVENTION

It is the object of the present invention to provide oral care products which can be used for improving the oral hygiene of humans and animals, by effectively preventing the formation of dental plaque and/or removing already deposited dental plaque.

The present inventors have seen indications that Starch Binding Domains (SBDs), known to have affinity for binding specifically to starch, disperse polysaccharides. Due to this dispersing effect SBDs are suitable for removing and/or preventing the formation of dental plaque.

This is surprising as a person skilled in the art of dental science would not expect that SBDs have a dental plaque removing and/or preventing effect, as SBDs are generally believed to have no or a lower affinity for oral polysaccharides which do not comprise significant amounts of starch (i.e. amylose or amylopectin which are polysaccharides of glucose residues joined by α-1,4-linkages (amylose) and α-1,4-linkages with α-1,6-linkages (amylopectin)).

In the present context ". . . a lower binding affinity . . . " means that the binding affinity of SBDs for non-starch polysaccharides, such as dextran and mutan constituting oral polysaccharides, is lower than the binding affinity for starch.

Without being limited to any theory the inventors believe that the dental plaque removing and/or preventing effect of SBDs is due to dispersion of the oral polysaccharide resulting in dissolution or at least disruption of the polysaccharides of dental plaque. This facilitates the removal of the dental plaque when e.g. brushing the teeth, rinsing the mouth with a mouth wash or the like.

In the first aspect the invention relates to an oral care composition comprising an SBD and further ingredients conventionally used in oral care compositions.

In a preferred embodiment the SBD is a Single Unit SBD as defined above.

In another embodiment of the invention the oral care composition comprises a fusion product between one or more SBDs and one or more enzymes selected from the group including oxidases, peroxidases, proteases, lipases, glycosidases, lipases, esterases, deaminases, ureases and polysaccharide hydrolases, preferably α-glycosidases, especially mutanases, dextranases, pullulanases, or α-amylases.

Any SBD may be used. Specifically contemplated are SBDs from glucoamylases, such as the above mentioned SBD from an *A. niger* glucoamylase.

In a specific example the SBD, as SBD-enzyme hybrid or Single Unit SBD, is a region (E-domain or D+E Domain shown in SEQ ID Nos. 2 and 4) in the maltogenic amylase enzyme product produced by *Bacillus stearothermophilus* C599 disclosed in EP patent no. 120,693 (Novo Industri A/S).

The inventors have also found that SBDs advantageously can be used in combination with an enzyme activity capable of degrading the polysaccharides of dental plaques.

The Action of SBDs

Efficient enzymatic degradation requires a tight interaction between a substrate and an enzyme. Further, it is known that SBDs enhance enzyme activities as the local enzyme concentration on the substrate surface to which it can bind (i.e. mainly starch) is increased.

However, it is surprising that SBDs enhance the activity of enzymes acting on substrates to which SBDs are generally believed to have no or a lower affinity towards (i.e. non-starch carbohydrates), than to starch.

Consequently, in a preferred embodiment the oral care composition comprises an SBD and an enzyme capable of degrading oral care polysaccharides.

Preferred enzymes are glycosidases capable of hydrolyzing glycosidic linkages and thereby capable of degrading oral polysaccharides.

All glycosidases within E.C. 3.2. "Enzyme Nomenclature (1992), Academic Press, Inc.". are contemplated according to the invention and are hereby incorporated by reference.

When combining an SBD with an enzyme capable of degrading oral polysaccharides a synergistic effect is obtained. It is believed that the SBD provides access to the substrate (i.e. the oral polysaccharides) enabling an intimate association and proximity (i.e. a tighter interaction) between the enzyme and its substrate. This results in a faster degradation of the dental plaque or renders it possible to use less enzyme to obtain the desired result.

Preferred glycosidases are α-glycosidases, especially α-glycosidases selected from the group of dextranases, mutanases, pullulanases, α-amylases, and mixtures thereof.

The dextranase may be derived from a strain of the genera Penicillium, Paecilomyces, Aspergillus, Fusarium, Spicaria, Verticillium, Helminthosporium and Chaetomium; bacteria of the genera Lactobacillus, Streptococcus, Cellvibrio, Cytophaga, Brevibacterium, Pseudomonas, Corynebacterium, Arthrobacter and Flavobacterium, and yeasts such as *Lipomyces starkeyi*. Specifically contemplated is dextranase derived from a strain of *Paecilomyces lilacinum*.

The mutanase may be derived from a strain of the genera Trichoderma, Streptomyces, Cladosporium, Bacillus, or Aspergillus. Specifically contemplated is mutanases derived from *T. harzianum*, especially the deposited strain *T. harzianum* CBS 243.71.

The α-amylase may be derived from a strain of the genus Bacillus, in particular a strain of *B. licheniformis*, described in more detail in GB 1,296,839.

The oral care composition may further comprise one or more enzymes, which may be recombinant, selected from the group including oxidases, peroxidases, proteases, lipases, other glycosidases, lipases, esterases, deaminases, ureases, polysaccharide hydrolases, and mixtures thereof.

The oral care composition may further comprise agents adding an additional property to the oral care composition.

Such additional agents include other anti-plaque agents, anti-staining agents, anti-microbial agents, antibodies, antibody fragments, histamins, lactoferins, defensins, magainins, cecropins, other cationic anti-bacteriocins, bacteriocins, microbicides including, but not limited to, triclosan, chlorhexidine, quaternary ammonium compounds, chloroxylenol, chloroxyethanol, thymol, fluoride, antimicrobial cations such as Zn, Sn, and Cu.

An oral care composition of the invention may suitably have incorporated an amount of 0.001–10 mg/ml SBD calculated on the basis of final oral care product.

When adding glycosidases to the oral care composition these may constitute from 0.0001% to 20%, preferably 0.001% to 5% of the final oral care product.

In the case of the glycosidase(s) being a dextranase, a mutanase, and/or a pullulanase, respectively, they may, independent of each other be added in amounts equivalent to an enzyme activity, calculated as enzyme activity units in the final oral care product, in the range from 0.001 KDU to 1000 KDU/ml, preferably from 0.01 KDU/ml to 500 KDU/ml, especially from 0.1 KDU/ml to 100 KDU/ml for dextranases, and/or from 0.001 MU/ml to 1000 MU/ml, preferably from 0.01 MU/ml to 500 MU/ml, especially from 0.01 MU/ml to 100 MU/ml and from 0.01 MU/ml to 100 MU/ml, for mutanases, and/or in the range from 0.001 KPU to 1000 KPU/ml, preferably from 0.01 KPU/ml to 500 KPU/ml, especially from 0.1 KPU/ml to 100 KPU/ml for pullulanases.

It is preferred that the enzyme(s) is(are) substantially active at temperatures and pHs prevailing in the mouth when using the oral care product of the invention. This normally means that the enzymes should be substantially active between 20° C. and 40° C., and at pHs in the range from pH 4.0 to 8.0.

The term "substantially active" means in the context of the present invention that the enzyme in question has a relative activity above 70%, in particular above 80%, and especially above 90% of the activity at the temperature optimum.

Oral Care Products

The invention also relates to oral care products comprising an oral care composition of the invention. The oral care product may have any suitable physical form (i.e. powder, paste, gel, liquid, ointment, tablet etc.).

An "oral care product" can be defined as a product which can be used for maintaining or improving the oral hygiene in the mouth of humans and animals, by preventing formation of dental plaque, removing dental plaque, preventing and/or treating dental diseases, etc.

At least in the context of the present invention oral care products do also encompass products for cleaning dentures, artificial teeth and the like.

Examples of such oral care products include toothpaste, dental cream, gel or tooth powder, odontic, mouth washes, pre- or post brushing rinse formulations, chewing gum, lozenges, and candy.

Toothpastes and tooth gels typically include abrasive polishing materials, foaming agents, flavoring agents, humectants, binders, thickeners, sweetening agents, whitening/bleaching/stain removing agents, water, and optionally enzymes.

Mouth washes, including plaque removing liquids, typically comprise a water/alcohol solution, flavor, humectant, sweetener, foaming agent, colorant, and optionally enzymes.

Abrasive polishing material might also be incorporated into the dentifrice product of the invention. According to the invention said abrasive polishing material includes alumina and hydrates thereof, such as alpha alumina trihydrate, magnesium trisilicate, magnesium carbonate, kaolin, aluminosilicates, such as calcined aluminum silicate and aluminum silicate, calcium carbonate, zirconium silicate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels and the like. Also suitable as abrasive agents are calcium pyrophosphate, water-insoluble alkali metaphosphates, dicalcium phosphate and/or its dihydrate, dicalcium orthophosphate, tricalcium phosphate, particulate hydroxyapatite and the like. It is also possible to employ mixtures of these substances.

Dependent on the oral care product the abrasive product may be present in from 0 to 70% by weight, preferably from 1% to 70%. For toothpastes the abrasive material content typically lies in the range of from 10% to 70% by weight of the final toothpaste product.

Humectants are employed to prevent loss of water from e.g. toothpastes. Suitable humectants for use in oral care products according to the invention include the following compounds and mixtures thereof: glycerol, polyol, sorbitol, polyethylene glycols (PEG), propylene glycol, 1,3-propanediol, 1,4-butanediol, hydrogenated partially hydrolyzed polysaccharides and the like. Humectants are in general present in from 0% to 80%, preferably 5 to 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which help stabilizing the dentifrice product. Thickeners may be present in toothpaste creams and gels in an amount of from 0.1 to 20% by weight, and binders to the extent of from 0.01 to 10% by weight of the final product.

As foaming agent soap, anionic, cationic, non-ionic, amphoteric and/or zwitterionic surfactants can be used. These may be present at levels of from 0% to 15%, preferably from 0.1 to 13%, more preferably from 0.25 to 10% by weight of the final product.

Surfactants are only suitable to the extent that they do not exert an inactivation effect on the present SBDs/enzymes. Surfactants include fatty alcohol sulphates, salts of sulphonated mono-glycerides or fatty acids having 10 to 20 carbon atoms, fatty acid-albumen condensation products, salts of fatty acid amides and taurines and/or salts of fatty acid esters of isethionic acid.

Suitable sweeteners include saccharin.

Flavors, such as spearmint, are usually present in low amounts, such as from 0.01% to about 5% by weight, especially from 0.1% to 5%.

Whitening/bleaching agents include $H_2O_2$ and may be added in amounts less that 5%, preferably from 0.25 to 4%, calculated on the basis of the weight of the final product.

Water is usually added in an amount giving e.g. toothpaste in a flowable form.

Further water-soluble anti-bacterial agents, such as chlorhexidine digluconate, hexetidine, alexidine, quaternary ammonium anti-bacterial compounds and water-soluble sources of certain metal ions such as zinc, copper, silver and stannous (e.g. zinc, copper and stannous chloride, and silver nitrate) may also be included.

Also contemplated according to the invention is the addition of compounds which can be used as fluoride source, dyes/colorants, preservatives, vitamins, pH-adjusting agents, anti-caries agents, desensitizing agents, etc.

Other essential components used in oral care products and in oral care products of the invention are enzymes. Enzymes are biological catalysts of chemical reactions in living systems. Enzymes combine with the substrates on which they act forming an intermediate enzyme-substrate complex. This complex is then converted to a reaction product and a liberated enzyme which continues its specific enzymatic function.

Enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids which form the structural components of bacterial cell walls and membranes. Dextranase breaks down the organic skeletal structure produced by bacteria that forms a matrix for bacterial adhesion. Proteases and amylases not only prevent plaque formation, but also prevent the development of calculus by breaking up the carbohydrate-protein complex that binds calcium, thereby preventing mineralization.

A toothpaste produced from an oral care composition of the invention (in weight % of the final toothpaste) may typically comprise the following ingredients:

| | |
|---|---|
| Abrasive material | 10 to 70% |
| Humectant | 0 to 80% |
| Thickener | 0.1 to 20% |
| Binder | 0.01 to 10% |
| Sweetener | 0.1% to 5% |
| Foaming agent | 0 to 15% |
| Whitener | 0 to 5% |
| Enzymes | 0.0001% to 20% |
| Starch Binding Domain | 0.0001% to 1% |

A mouth wash produced from an oral care composition of the invention (in weight % of the final mouth wash product) may typically comprise the following ingredients:

| | |
|---|---|
| 0–20% | Humectant |
| 0–2% | Surfactant |
| 0.0001%–5% | Enzymes |
| 0.0001%–1% | Starch Binding Domain |
| 0–20% | Ethanol |
| 0–2% | Other ingredients (e.g. flavor, sweetener, active ingredients such as flourides) |
| 0–70% | Water |

The mouth wash composition may be buffered with an appropriate buffer, e.g. sodium citrate or phosphate in the pH-range 6–7.5.

The mouth wash may be in non-diluted form (i.e. must be diluted before use).

The "enzymes" referred to in connection with the specific toothpaste and mouth wash above include glycosidases, preferably α-glycosidases, especially dextranase, mutanase, pullulanase, and α-amylase described above, and optionally other types of enzymes mentioned above known to be used in oral care products.

Method of Manufacture

The oral care composition and products of the present invention can be made using methods which are common in the oral product area.

Finally the invention relates to the use of an SBD for oral care purposes, such as removing and/or preventing dental plaque formation in the oral cavity of humans or animals.

In a preferred embodiment the SBD is a Single Unit SBD as defined above.

In a preferred embodiment the use of an SBD is combined with one or more enzyme(s) selected from the above mentioned group of enzymes.

MATERIALS AND METHODS

Microorganisms:
*Streptococcus sobrinus* strain CBS 350.71 (or OMZ 176)
*Actinomyces viscosus* DSM 43329
*Fusobacterium nucleatum* subsp. polymorphum DSM 20482
*Bacillus stearothermophilus* C599 (EP 120,683) comprising the maltogenic amylase E and D-domain.
*Bacillus subtilis* DN1885 (Diderichsen et al., Journal of Bacteriology, vol. 172, p. 4315–4321, 1990)

Enzymes:
Dextranase produced by *Paecilomyces lilacinum* (available from Novo Nordisk A/S).
Mutanase produced by *Trichoderma harzianum* CBS 243.71 (available from Novo Nordisk A/S)

Solutions
Britton-Robinson Buffer
Erythrosin B (Sigma)

Equipment
Shaker (Eppndorf Thermomixer, Type 5436)
Chromameter CR-200 (Minolta)

Plasmids
pDN1981 (P. L. Jorgensen, C. K. Hansen, G. B. Poulsen and B.Diderichsen (1990) In vivo genetic engineering: homologues recombination as a tool for plasmid construction, Gene, 96, p37–41.)

Methods
Preparation of Mutan
Mutan is prepared by growing Streptococcus mutans CBS 350.71 at pH 6.5, 37° C. (kept constant), and with an aeration rate of 75 rpm in a medium comprised of the following components:

| | |
|---|---|
| NZ-Case | 6.5 g/liter |
| Yeast Extract | 6 g/liter |
| $(NH_4)_2SO_4$ | 20 g/liter |
| $K_2PO_4$ | 3 g/liter |
| Glucose | 50 g/liter |
| Pluronic PE6100 | 0.1% |

After 35 hours, sucrose is added to a final concentration of 60 g/liter to induce glycosyltransferase. The total fermentation time is 75 hours. The supernatant from the fermentation is centrifuged and filtered (sterile). Sucrose is then added to the supernatant to a final concentration of 5% (pH is adjusted to pH 7.0 with acetic acid) and the solution is stirred overnight at 37° C. The solution is filtered and the insoluble mutan is harvested on propex and washed extensively with deionized water containing 1% sodium benzoate, pH 5 (adjusted with acetic acid). Finally, the insoluble mutan is lyophilized and ground.

Determination of Dextranase Activity (KDU)
One Kilo Novo Dextranase Unit (1 KDU) is the amount of enzyme which breaks down dextran forming reducing sugar equivalent to 1 g maltose per hour in Novo Nordisk's method for determination of dextranase based on the following standard conditions:
Substrate . . . Dextran 500 (Pharmacia)
Reaction time . . . 20 minutes
Temperature . . . 40° C.
pH . . . 5.4
A detailed description of Novo Nordisk's analytical method (AF 120) is available on request.
Determination of Mutanase Activity (MU)
One Mutanase Unit (MU) is the amount of enzyme which under standard conditions liberates 1 mmol reducing sugar (calculated as glucose) per minute.
Standard Conditions
Substrate . . . 1.5% mutan
Reaction time . . . 15 minutes
Temperature . . . 40° C.
pH . . . 5.5
A detailed description of Novo Nordisk's analytical method (AF 180/1-GB) is available from Novo Nordisk A/S on request.
Preparation of Hydroxyapatite Disks (HAP disks)
Hydroxyapatite disks are prepared by compressing 250 mg of hydroxyapatite in a disk die at about 5,900 kg (13,000 lbs) of pressure for 5 minutes. The disks are then sintered at 600° C. for 4 hours.
Assessment of the Plaque Removing Effect
The method used for assessing the plaque removal effect is based on the method described by Kao in JP2250816. According to the present method the hydroxyapatite disks (HAP disks) are coated with a biofilm comprising three strains of oral microorganisms (*Streptococcus sobrinus, Actinomyces viscosus* and *Fusobacterium nucleatum*).

To test the plaque removing and preventing effect 0.1% Erythrosin B in PBS is used to stain plaque present on the hydroxyapatite disks red. The intensity of the red color (i.e. a*) is measured on a Chromameter CR-200. The max. a* value is 60. Values below that indicate a less intensive red color (i.e. less plaque present). If the a*-value is determined to be zero, no red color is present (i.e. no plaque).
General Molecular Biology Methods:
DNA manipulations and transformations were performed using standard methods of molecular biology (Sambrook et al. (1989) Molecular cloning: A laboratory manual, Cold Spring Harbor lab., Cold Spring Harbor, NY; Ausubel, F. M. et al. (eds.) "Current Protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

EXAMPLES

Example 1

Construction of a SBD Expression Vector

Oligonucleotide PCR primers were designed to attempt to express either the E-domain alone or the D+E domain part of the AmyM (Novamyl) protein described in EP 120,693. The rationale was to add the signal sequence of the *Bacillus licheniformis* α-amylase (AmyL, Termamyl) in front of these AmyM fragments in attempts to have the proteins secreted from Bacillus.
The following primers were used:
110755:
PstI
5'-G ATG CTG CAG CAG CGG CG
TCCGCTTCAGCGCCGC-3' (the underscored region corresponds to pos. 1783–1798 in the amyM sequence, Genbank Accession nb. M36539)
110756:
PstI
5'-G ATG CTG CAG CAG CGG CG
AGTGGAACGCAGACATCG-3' (the underscored region corresponds to pos. 2032–2049 in the amyM sequence, Genbank Accession nb. M36539)
110757:
EcoRI BamHI
5'-G ATG GAA TTC GGA TCC T
CCATATGTACTACTCC-3' (the underscored region corresponds to pos. 2569–2553 in the amyM sequence, Genbank Accession nb. M36539)
Template for the PCR reaction was a sample of plasmid pDN1413. This is essentially plasmid pUB110 containing the amyM gene fragment, derived from the deposited strain NCIB 11837 via plasmid pDN452 which is described in EP 120,693.
Conditions for the PCR amplification were the following: 94° C. for 2 minutes, then 20 cycles of 49° for 30 seconds, 43° C. for 1 minute, 72° C. for 2 minutes, then one cycle of 72° C. for 5 minutes.
Correctly sized PCR fragments were obtained upon amplification. Primer #110755 together with #110757 resulted in a 820 basepair fragment, primer #110756 together with #110757 resulted in a 571 basepair fragment.
PCR fragments were purified using a QIAquick PCR Purification Kit Cat. No. 28106 from Qiagen, and digested with EcoRI+PstI.
Plasmid pDN1981 (P. L. Jørgensen et al. (1990), Gene, 96, p. 37–41) was used as cloning vector. pDN1981 was digested with EcoRI+PstI, and the 3.9 kb fragment purified from an agarose gel. The vector fragment was ligated with each of the digested PCR fragments, and the ligation mixtures transformed into competent cells of *Bacillus subtilis* DN1885 (Diderichsen et al., Journal of Bacteriology, vol. 172, p. 4315–4321, 1990), selecting kanamycin resistance (10 μg/ml). Four colonies from each transformation were reisolated and grown in liquid TY cultures for plasmid preparation. The extracted plasmids all had the correct structure, as judged by restriction digests.
Two transformants of each kind were kept:
SJ4302 and SJ4303 both contained plasmids harboring the #110755+#110757 PCR fragment, i.e. encoding the D+E domain.
SJ4304 and SJ4305 both contained plasmids harbouring the #110756+#110757 PCR fragment, i.e. encoding the E-domain only.
Expression of Domains:
Strains SJ4302-SJ4305 were inoculated in 10 ml TY broth containing 0.4 % glucose and 10 μ/ml kanamycin, and incubated at 37° C. with shaking for two days. Strain DN1885 (the *B. subtilis* host strain) was inoculated in 10 ml TY broth with 0.4% glucose, and incubated at 37° C. with shaking for two days.
Supernatants were analyzed by SDS-Polyacrylamide gel electrophoresis.
In the supernatant from strain SJ4302, a protein with an apparent molecular weight of approximately 25 kDa was observed. It was less obvious that SJ4303 produced a similar protein. This protein was not seen in the other 3 samples. The difference between SJ4302 and SJ4303 may be due to these clones harboring PCR amplified constructs that were not verified by DNA sequencing—an error might thus have been introduced into the SJ4303 clone.

In the supernatant from strains SJ4304 and SJ4305, a protein with an apparent molecular weight of approximately 10 kDa was observed. This protein was not observed in the other three samples.

In conclusion, a protein as expected was produced from the D+E domain clone SJ4302, and a protein as expected was produced from the E domain clones SJ4304-SJ4305. No difference in expression level (amount of accumulated domain) was observed when the strains were simply propagated as above, or when the strains were propagated in broth as above, but supplemented with the protease inhibitor Complete from Boehringer Mannheim (CompleteTM Protease inhibitor cocktail tablets Cat. No. 1697498; One tablet was dissolved in 2 ml water, and 160 microliters of this solution added to each 10 ml culture). This concentration of protease inhibitor allowed growth, but almost totally inhibited the extracellular proteases present in the DN1885 broth, as judged from spotting broth on agar plates with casein.

Example 2

Plaque Inhibition

Hydroxyapatite disks are sterilized at 180° C. for 2 hours before incubated with the sterilized saliva at 37° C. overnight. The hydroxyapatite disks are then placed at the bottom of Nunclon™ wells (4×6 wells, Ø 150 mm), where three oral bacteria, *Streptococcus sobrinus* CBS 350.71, *Actinomyces viscosus* DSM 43329 and *Fusobacterium nucleatum* DSM 20482 are inoculated in Brain heard infusion medium containing 0.2% sucrose (total volume: 2.0 ml). The oral bacteria are cultivated under anaerobic conditions for 16 hours at 37° C.

After cultivation, the disks are rinsed briefly with PBS. Then they are incubated in a 1 ml 0.1% Erythrosin B in PBS for 1 minute. The Erythrosin B solution is taken out by means of suction and the disks are washed with 2.0 ml PBS for a few minutes. Afterwards the disks are dried in air overnight at room temperature, a* is measured with a Chromameter (Minolta).

The dental plaque preventing effect is tested using the samples shown in Table 1.

TABLE 1

|   | SBD µg protein/ml | Mutanase/Dextranase |
|---|---|---|
| 1 | 0 | 0 |
| 2 | 96 | 0 |
| 3 | 0 | 1 MU/ml + 1 kDU/ml |
| 4 | 48 | 1 MU/ml + 1 kDU/ml |

What is claimed is:

1. An oral care composition comprising a polypeptide consisting of Starch Binding Domain (SBD), wherein said SBD is derived from a microorganism and said composition is selected from the group consisting of a toothpaste, dental cream, gel or tooth powder, odontic, mouthwash, pre- or post brushing rinse formulation, chewing gum, lozenge, and candy.

2. The oral care composition according to claim 1, wherein the SBD is a Single Unit SBD.

3. The oral care composition according to claim 2, wherein the SBD is the E-domain or the DE-domain of the maltogenic amylase enzyme product produced by *Bacillus stearothermophilus* C599.

4. The oral care composition according to claim 1, further comprising an enzyme selected from the group consisting of oxidases, peroxidases, proteases, lipases, glycosidases, lipases, esterases, deaminases, ureases and polysaccharide hydrolases.

5. The oral care composition according to claim 1, further comprising a fusion product between one or more SBDs and an enzyme selected from the group consisting of oxidases, peroxidases, proteases, lipases, lipases, esterases, deaminases and ureases.

6. The oral care composition according to claim 1, wherein the composition further comprises an anti-plaque agent, anti-staining agent, or anti-microbial agent.

7. An oral care product comprising the oral care composition of claim 1.

8. A method for the prevention of dental plaque formation on teeth and/or removal of dental plaque from teeth, said method comprising contacting teeth with an effective amount of an oral care composition according to claim 1.

* * * * *